United States Patent

Avendaño Lopez et al.

Patent Number: 5,716,963
Date of Patent: Feb. 10, 1998

[54] ANTHRAQUINONIC DERIVATIVES HAVING AN ANTITUMOR ACTIVITY AND APPLICATIONS THEREOF

[75] Inventors: Carmen Avendaño Lopez; Dolores Garcia Gravalos, both of Madrid, Spain

[73] Assignee: Universidad Complutense De Madrid, Madrid, Spain

[21] Appl. No.: 535,174

[22] PCT Filed: Feb. 24, 1995

[86] PCT No.: PCT/ES95/00024

§ 371 Date: Mar. 27, 1996

§ 102(e) Date: Mar. 27, 1996

[87] PCT Pub. No.: WO95/23145

PCT Pub. Date: Aug. 31, 1995

[30] Foreign Application Priority Data

Feb. 24, 1994 [ES] Spain ................... 9400366

[51] Int. Cl.$^6$ ............... C07D 221/06; C07D 471/04; A61K 31/44; A61K 31/45
[52] U.S. Cl. ............ 514/290; 514/292; 546/79; 546/81
[58] Field of Search .......... 546/81, 79; 514/292, 514/290

[56] References Cited

U.S. PATENT DOCUMENTS 1,882,867 10/1932 Ochs .................... 424/75
1,942,407 3/1934 Black .................... 424/75
4,300,243 11/1981 Baumgartner ............ 623/11

FOREIGN PATENT DOCUMENTS 322366 2/1902 France.
5305126 11/1993 Japan.

*Primary Examiner*—Alan L. Rotman
*Attorney, Agent, or Firm*—Klauber & Jackson

[57] ABSTRACT

Said derivatives have the general formula (I) and are:

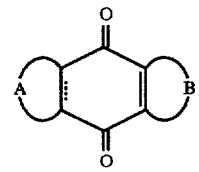

(I-A) 4,6,7-trimethyl-5,8,8a,10a-tetrahydro-1H-1-azaanthracen-2,9,10-trione; (I-B) 2-ethoxy-3-methyl-1-azaanthracen-9,10-dione; (I-C) 3-ethyl-1,8-dihydro-1H-1,8-diazaanthracen-2,7,9,10-tetraone; (I-d) 2-acethoxy-3-methyl-1,8-diazaanthracen-2,9,10-trione; (I-e) 6-fluor-4-methyl-1H-1,8-diazaanthracen-2,9,10-trione; (I-f) 6-dimethylamino-4-methyl-1H-1,8-diazaanthracen-2,9,10-trione; (I-g) 4-methyl-5-(2-nitrophenyl)-5,8-dihydro-1H-1,8-diazaanthracen-2,9,10-trione; (I-h) 3,5-dimethyl-1,8-dihydro-1,8-diazaanthracen-2,7,9,10-tetraone; (I-i) 3,6-difluor-1,8-diazaanthracen-9,10-dione; (I-j) 6-methyl-3-phenyl-1H-1,8-diazaanthracen-2,9,10-trione; (I-k) 3-fluor-4-methyl-1-dihydro-1-azaanthracen-9,10-dione; 3-fluor-1-azaanthracen-1,10-dione. Application as antitumor agents.

23 Claims, No Drawings

ANTHRAQUINONIC DERIVATIVES HAVING AN ANTITUMOR ACTIVITY AND APPLICATIONS THEREOF

CROSS-REFERENCE

This application is a 371 of PCT/ES95/00024.

TECHNICAL FIELD OF THE INVENTION

The present invention fits in the technical field of products with antitumor activity, used to make medicines to treat cancer in the different manifestations thereof.

More specifically, the present invention refers to a series of new anthraquinonic derivatives with important antitumor activity.

PRIOR ART OF THE INVENTION

Diazaquinomycin A is a 1,8-diazaanthraquinone found during the routine study of secondary metabolites coming from bacteria (S. Omura et al., J. Antibiotics, 35, 1425 (1982); and S. Omura et al. Tetrahedron Letters, 24, 3643 (1963)). Said product, which has the following formula (1)

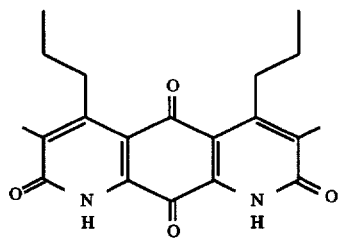

shows goods activity against Gram positive bacteria, due to its capacity to inhibit thymidilate synthetase (S. Omura et al., J. Antibiotics, 38, 1016 (1985); and M. Murata et al. T. Miyasaka, H. Tanaka, S. Omura, J. Antibiotics, 38, 1025 (1985)). However, Diazaquinomycin is inactive as an antitumor agent.

Japanese patent no. 63 79.830 describes Diazaquinomycin derivatives of formulae (2) and (3):

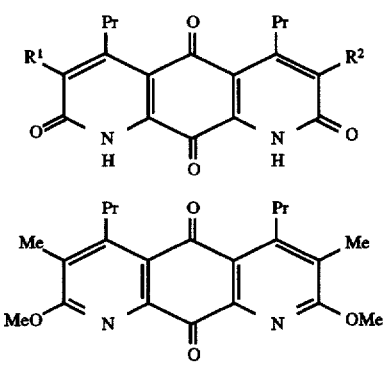

wherein $R^1$ and $R^2$ have, among others, the meanings $(CH_2)_nCO_2R^3$, $CH_2CH(CO_2^3)_2$, etc. or else one of $R^1$ and $R^2$ is methyl and the other is $(CH_2)_nCO_2R^3$, $CO_2CH(CO_2R^3)_2$, etc. n being=0–2 and $R^3$=hydrogen or $C_{1-6}$ alkyl, that have shown usefulness as anticarcinogenic and antibacterial agents.

The compounds of formulae (4), (5), (6) and (7) (Omura, J. Antibiotics, 42, 727, 1989):

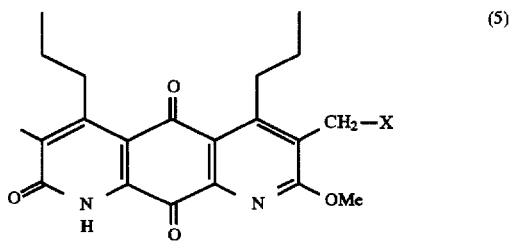

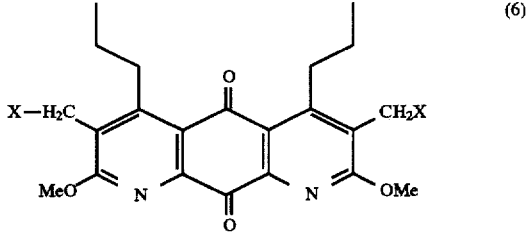

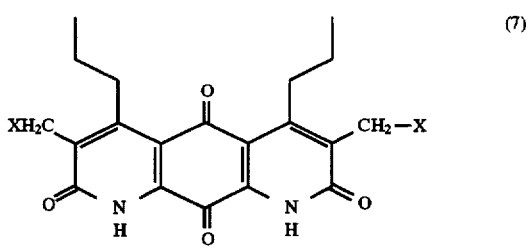

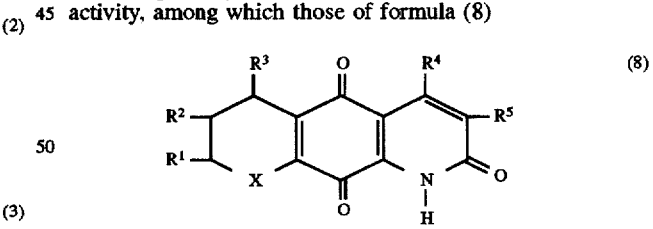

X=H, BNr, OH, CN, $CH(CO_2Et)_2$
which have shown antitumor activity in cytotoxicity studies and in vitro studies, have also been described.

On the other hand, the applicant has studied large amounts of Diazaquinomycin derivatives that have shown antitumor activity, among which those of formula (8)

described in British patent application no. 9212000.5 of 5 Jun. 1992, that also have antitumor activity, also deserve special mention.

Following along these lines, the present invention provides new anthraquinonic derivatives with important antitumor activity.

DETAILED DESCRIPTION OF THE INVENTION

The present invention relates to new anthraquinonic derivatives with antitumor activity and to the applications thereof.

The new compounds provided by the present invention correspond to the general formula (I)

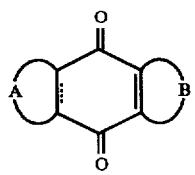

(I)

wherein the broken line represents a double bond that may or may not be present and A and B form, together with the center ring, an anthraquinonic system that responds to the following pairs of meanings of A and B:

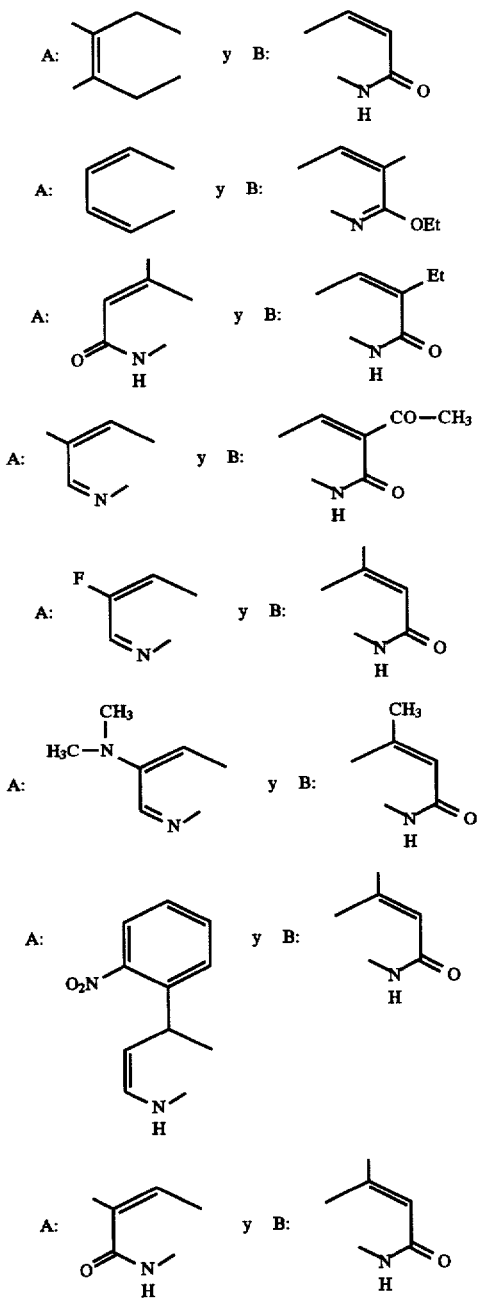

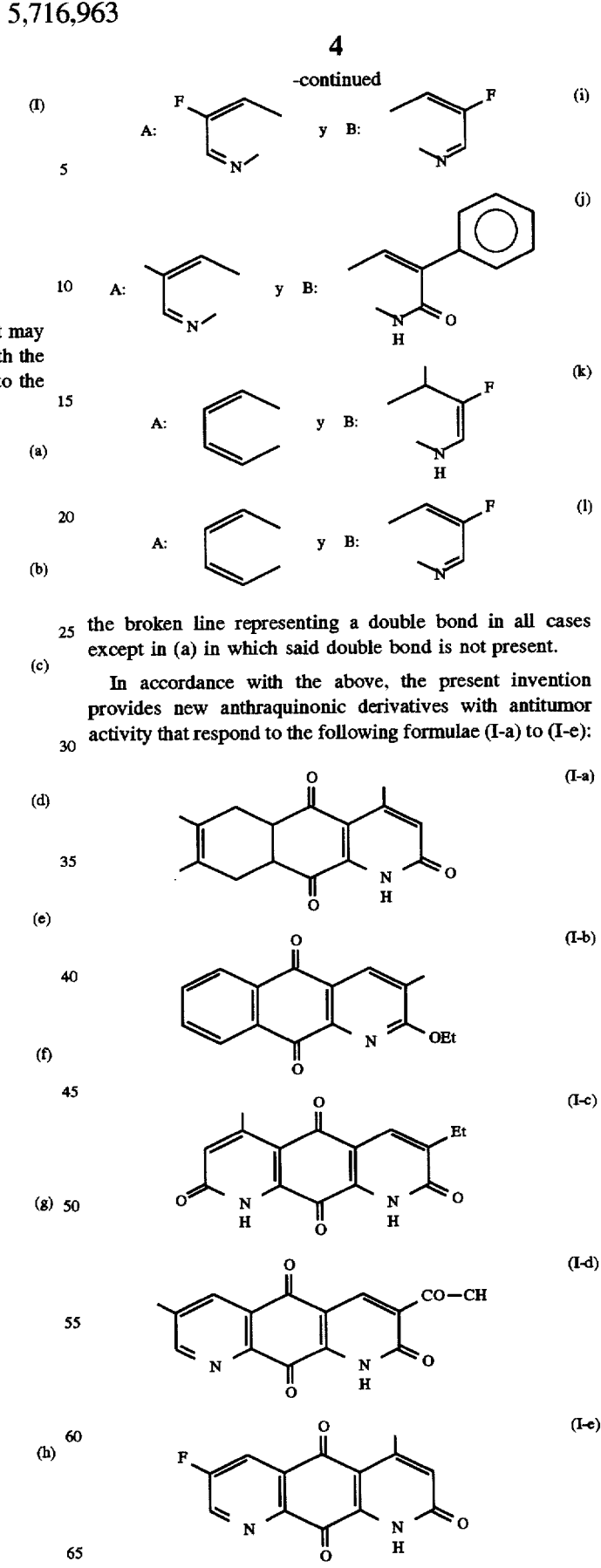

the broken line representing a double bond in all cases except in (a) in which said double bond is not present.

In accordance with the above, the present invention provides new anthraquinonic derivatives with antitumor activity that respond to the following formulae (I-a) to (I-e):

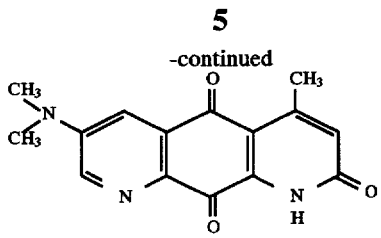
(I-f)

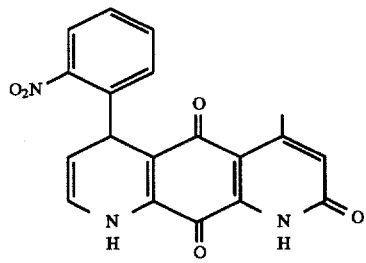
(I-g)

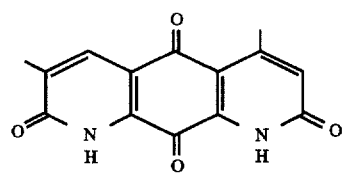
(I-h)

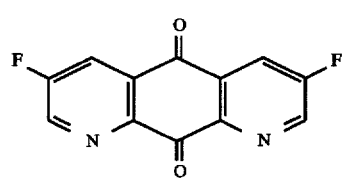
(I-i)

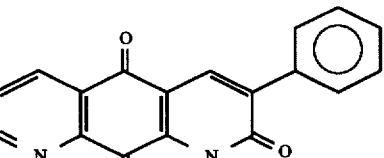
(I-j)

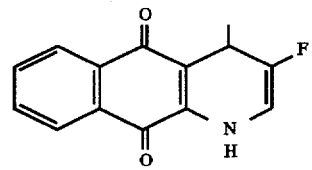
(I-k)

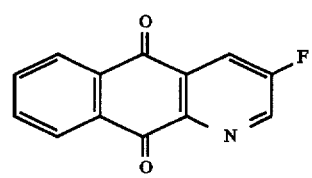
(I-l)

The present invention also provides pharmaceutical compositions that comprise one or more compounds of formula (I-a) to (I-1) in association with a solvent or pharmaceutically acceptable carrier.

The invention additionally provides the use of one or several of the compounds of formulae (I-a) to (I-1) in the manufacture of an antitumor drug. Finally, the invention provides a method to treat tumors using the compounds of formulae (I-a) to (I-1).

The compounds of the present invention are characterized in that they have excellent antitumor activity, as can be inferred from the biological activity studies carried out with the same and that are set forth hereinafter.

EMBODIMENTS OF THE INVENTION

The present invention is additionally illustrated by means of the following Examples, which do not seek to be restrictive of the scope hereof.

EXAMPLE 1

Preparation of 4,6,7-trimethyl-5,8,8a,10a-tetrahydro-1H-1-azaathracen-2,9,10-trione (I-a)

A solution of 4-methyl-1H-quinolin-2,5,8-trione (223 mg., 1.2 mmol) and 2,3-dimethyl-1,3-butadiene (106 mg, 1.3 mmol) was heated in ethyl acetate (130 ml), at 100° C. for 12 hours in a closed 250 ml. flask. The cooled solution was evaporated at reduced pressure and the residue was chromatographed on silica gel, eluting with dichloromethane-ethyl acetate (6:4) to give 153 mg. (48%) of (I-a). m.p. 285°–288° C. (ethyl acetate).

Spectroscopic data for compound (I-a):

IR (Kbr): 3260–2800 (N-H), 1660 (C=O) $cm^{-1}$ $^1$H-NMR (300 Mhz. $CDCl_3$) 9.80 (b.s. 1H. NH). 6.64 (d 1H J=1.2 Hz. $C_3$-H): 3.33 (m.2H. $C_{8a}$-H and $C_{1a}$-H); 2.53 (d 3H J=1.2 Hz $C_3$—CH) 2.42 (m 2H $C_5$-$H_{ax}$ and $C_8$-$H_{ax}$); 2.15 (m, 2H, $C_5$-$H_{eq}$ and $C_8$-$H_{eq}$); 1.64 (s.6H. $C_{6,7}$—$CH_3$) ppm $^{13}$C-NMR (75.4 Mhz. $CDCl_3$): 196.18 ($C_9$), 192.68 ($C_{10}$, 160.18 ($C_2$) 152.15 ($C_4$) 140.18 ($C_9$) 127.86 ($_3$), 123.68 ($C_6$) 123.18 ($C_7$) 118.20 ($C_4$) 47.76 ($C_{8a}$) 46.09 ($C_{10a}$) 30.70 and 30.46 ($C_5$ and $C_8$) 21.98 ($C_4$—$CH_3$). 18.82 ($C_6$—$CH_3$ and $C_7$—$CH_3$) ppm.

EXAMPLE 2

Preparation of 2-ethoxy-3-methyl-1-azaanthracen-9,10-dione (I-b)

5 portions of 0.08 g (0.42 mmol of tosyl chloride were added to an agitated solution of 100 mg. (0.42 mmol) of 3-methyl-1-azaanthracen-9,10-dione 1-oxide in absolute ethanol at 75°–78° C. for 1 hour. Then the mixture was agitated at room temperature overnight and a yellow solid (58 mg, 0.22 mmol) corresponding to the compound (I-b) (yield 52%) was filtered. The starting product was recovered from the water by means of silica gel column chromatography eluting with ethyl acetate: ethanol (9:1): m.p. 186°–188° C. (the sublime compound around 170° C.).

Spectroscopic data for compound (I-b):

IR(Kbr): 1685 and 1665 (C=O)$cm^{-1}$.

$^1$H-NMR (300 MHz. $CDCl_3$): 8.30 (m, 1H, $C_8$-H); 8.25 (m, 1H, $C_5$-H): 8.24 (d, 1H, J=0.8 Hz, $C_4$-H); 7.78 (m, 2H, $C_6$-H and $C_7$-H), 4.67 (q.2H.J=7.1 Hz, $CH_2$): 2.35 (d, 3H, J=0.8 Hz, $C_3$—$CH_3$); 1.48 (t, 3H, J-7.1 Hz. $CH_3$) ppm.

$^{13}$H-NMR (300 Mhz, $CDCl_3$); 182.6 ($C_9$); 181.8 ($C_{10}$); 165.5 ($C_2$); 146.1 ($C_{9a}$); 136.3 ($C_4$); 134.0 ($C_8$): 133.9 ($C_5$); 133.3 ($C_8$); 132.6 ($C_{10}$): 127.9 ($C_3$); 127.3 ($C_7$ or $C_6$); 126.8 ($C_6$ or $C_7$): 125.6 ($C_{4a}$); 63.3 ($CH_2$—$CH_3$); 16.4 ($C_3$—$CH_3$); 14.4 ($CH_3$—$CH_2$) ppm.

EXAMPLE 3

Preparation of 3-ethyl-1,8-dihydro-1H-1,8-diazaanthracen-2,7,9,10-tetraone (I-c)

a) A solution of 6-ethyl-4-methyl-1H-1,8-diazaanthracen-2,9,10-trione in trifluoroacetic acid (2 ml) and 30% hydrogen peroxide (1 ml) was agitated at 70° C. for 1 hour. Water (20 ml) was added and the cooled mixture was extracted with chloroform (75 ml), dried with $Na_2SO_4$ and was evaporated at reduced pressure. The residue (0.22 g) was chromatographed on silica gel eluting with dichloromethane-ethanol (9:1) yielding 125 mg. of 3-ethyl-5-methyl-1H-1,8-diazaanthracen-7,9,10-trione 1-oxide (60%). It was not possible to obtain the melting point because the N-oxide decomposed when it was heated.

Spectroscopic data of said N-oxide

IR (KBr): 3650–3300 (N-H); 1665 and 1650 (C=O)cm$^{-1}$.

$^1$H-NMR (250 MHz, CDCl$_3$); 8.37 (s, 1H, C$_4$-H); 7.93 (s, 1H, C$_2$-H); 6.66 (s, 1H, C$_6$-H); 2.78 (q, 2H, J=7.4 Hz, CH$_2$); 2.67 (s 3H C$_5$—CH$_3$); 1.37 (t 3H, J=7.4 Hz CH$_3$—CH$_2$) ppm.

$^{13}$-NMR (63 MHz, CDCl$_3$); 177.7 (C$_9$); 169.1 (C$_{10}$); 160.2 (C$_7$); 151.5 (C$_2$); 147.4 (C$_5$); 145.0 (C$_4$); 140.8 (C$_{8a}$); 134.3 ($_{9a}$); 133.4 (C$_{4a}$); 127.4 (C$_6$); 124.2 (C$_3$); 114.7 (C$_{10a}$); 26.5 (C$_5$—CH$_3$); 22.6 (CH$_2$); 14.5 (CH$_3$—CH$_2$) ppm.

b) 4 portions of 50 mg. of tosyl chloride were added at 1-hour intervals to a solution of 85 mg (0.30 mmol) of N-oxide in acetonitrile (25 ml) and water (4 ml). The solution was agitated at 70° C. for 20 hours, cooled at room temperature and agitated with water (10 mL.) Diethyl ether was added and the red precipitate was filtered and washed with ether, yielding 55 mg (65%) of compound (I-c) m.p.>300° C. (dec.).

Spectroscopic data for compound (I-c)

IR (KBr): 3700–3300 (N-H); 1680, 1655, 6645 (C=O) CM$^{-1}$.

$^1$H-NMR (250 Mhz, d$_6$-DMSO); 12.15 (s, 2H, N$_1$-H and N$_8$-H); 7.73 (s, 1H, C$_4$-H); 6.55 (s, 1H, C$_6$-H); 2.47 (m, 5H, CH$_2$ and C$_5$—CH$_3$; 1.11 (t, 3H, J=7.4 Hz, CH$_3$—CH$_2$) ppm.

$^{13}$-C-NMR (63 MHz ,d$_6$-DMSO); 180.6 (C$_9$); 173.8 (C$_{10}$); 161.7 (C$_7$); 161.0 (C$_2$) 151.5 (C$_5$); 141.3 (C$_3$); 136.3 (C$_4$); 130.1 ((C$_6$); 23.3 (CH$_3$—C$_4$) 21.9 (CH$_2$—CH$_3$); 12 1 (CH$_3$—CH$_2$) ppm. (C$_{4a}$, C$_{8a}$, C$_{9a}$ and C$_{10a}$ cannot be observed.

EXAMPLE 4

Preparation of 2-acetoxy-6-methyl-1,8-diazaanthracen-2,9,10-trione (I-d)

A solution of 154 mg (1,375 mmol) of 2-methylacrolein dimethylhydrazone in dry (6 ml) was added to 74 mg (0.34 mmol) of 3-acetyl-1H-quinolin-2,5,8-trione, under argon. The solution was agitated at 0° C. for 2 hours and evaporated to dryness at 0° C. The residue was washed with petroleum ether. Silica gel column chromatography of the residue, eluting with a gradient of pure dichloromethane up to pure ethyl acetate yielded 60 mg (62%) of the compound (I-d) m.p.>300° C.

Spectroscopic data for compound (I-d)

IR (KBr: 1680 and 1645 (C=O, CH$_3$CO) cm$_{-1}$.

$^1$H-NMR(300 MHz, d$_6$-DMSO); 12.85 (s, 1H, NH); 8.90 (d, 1H, J=1.7 Hz C$_7$—H); 8.45 (s 1H, C$_4$—H); 8.32 (d, 1H, J=1.7 Hz, C$_5$—H); 2.60 (s, 3H, CH$_3$); 2.51 (s, 3H, COCH$_3$) ppm.

EXAMPLE 5

Preparation of 6-fluoro-4-methyl-1H,1,8-diazaanthracen-2,9,10-trione (I-e) and of 6-dimethylamino-4-methyl-1H-1,8-diazaanthracen-2,9,10-trione (I-f)

A solution of 4-methyl-1H-quinolin-2,5,8-trione (650 mg., 3.4 mmol) and of 2-fluor-2-propenal-N,N-dimethylhydrazone (400 mg, 3.4 mmol) was refluxed for 2 days in dry chloroform. After evaporation of the solvent at reduced pressure, silica gel column chromatography eluted with ethyl acetate-ethanol (5:1) yielded 128 mg. (15%) of compound (I-e), 100 mg (11%) of compound (I-f) and 178 mg (23%) of 6-dimethylamino-4-methyl-1H-quinolin-2,5,8-trione). Both compounds (I-e) and (I-f) had a melting point higher than 350° C.

Spectroscopic data for compound (I-e):

IR (KBr): 3420 (N-H) 1645 (C=O) cm$^{-1}$.

$^1$H-NMR (250 MHz, CDCL$_3$); 8.89 (d, 1H, J=2.8 Hz, C$_7$-H); 8.21 (dd 1H J=2.8 and 7.7 Hz C$_5$-H; 6.73 (q not well resolved 1H, C$_3$-H) and 2.70 (d not well resolved 3H, C$_4$—CH$_3$) ppm.

$^{19}$F-NMR (250 MHz, CDCl$_3$); 112.7 (d, J=8 Hz) ppm.

$^{13}$C-NMR (63 MHz, d$_5$-pyridine); 180.1 (C$_9$) 176.1 (C$_{10}$), 161.9 (C$_2$), 161.8 (C$_6$, d, J=266.3 Hz), 150.1 (C$_4$), 143.4 (C$_7$, d, J=25.3 Hz), 143.5 ( a C$_8$ , d, J=5 HZ), 135.7 (C$_{9a}$), 132.9 (C$_{10}$ d J=4.6 Hz) 127.4 (C$_3$) 120.7 (C$_5$, d, J=19.9 Hz), 115.6 (C$_{4a}$) and 22.5 (C$_4$—CH$_3$) ppm.

Spectroscopic data for compound (I-f):

IR (KBr); 1650 (C=O) and 1570 cm$^{-1}$. H-NMR (250 MHz, CDCl$_3$): 8.42 (d, 1H, J=3.0 Hz, C$_7$-H); 7.53 (d, 1H, J=3.0 Hz, C$_5$-H); 6.62 (s, 1H, C$_3$-H); 3.27 (s, 6H, (CH$_3$)$_2$N and 2.68 (s, 3H, C$_4$—CH$_3$) ppm.

EXAMPLE 6

Preparation of 4-methyl-5-(2-nitrophenyl)-5,8-dihydro-1H-1,8-diazaanthracen-2,9,10-trione (I-g)

A solution of 4-methyl-1H-quinolin-2,5,8-trione (150 mg, 0.79 mmol) and of 2-nitrocinnamaldehyde (208 mg, 0.95 mmol) in chloroform (50 ml) was irradiated with ultrasound at 50° C. for 20 hours. The solution was evaporated to dryness and the residue was chromatographed over silica gel, eluting with a gradient of pure dichloromethane to dichloromethane:ethyl acetate 1:1, yielding 149 mg. of recovered diene, 45 mg. of compound (I-g) (174), 66 mg. of the starting quinone and 100 mg. of 6-dimethylamino-4-methyl-1H-quinolin-2,5,8-trione. m.p. 233°–236° C.

Spectroscopic data for compound (I-g)

IR (KBr): 3500 (N-H), 1665 (C=O) cm$^{-1}$.

$^1$H-NMR (250 MHz, pyridine-d$_5$) δ:10.66 (s, 1H, NH), 8.08 (m, 2H, C$_3$-H and C$_5$-H); 7.52 (t, 1H, J=7.6 Hz, C$_5$-H); 7.33 (t 1H J=7.6 Hz C$_4$-H); 6.68 (dd 1H, J=7.5 and 5.9 Hz); 6.61 (s, 1H, C$_3$-H), 5.67 (d, 1H, J=5.9 Hz, C$_5$-H); 2.29 (s 3H C$_4$—CH$_3$) ppm.

$^{13}$C-NMR (63 Mhz, pyridine-d$_5$) δ: 182.62 (C$_9$), 176.61 (C$_{10}$), 161.89 (C$_2$), 150.43 (C$_4$), 147.55 (C$_2$), 142.06 (C$_1$), 139.33 (C$_{8a}$), 138.63 (C$_{9a}$), 133.33 (C$_5$), 131.66 (C$_6$)l 127.07 (C$_3$), 126.53 (C$_7$), 124.54 (C$_4$), 123.56 (C$_3$) 114.25 (C$_{4a}$) 110.76 (C$_{10}$) 105.67 (C$_6$), 33.29 (C$_5$), 21.77 (C$_4$—CH$_3$) ppm.

EXAMPLE 7

Preparation of 3,5-dimethyl-1,8-dihydro-1,8-diazaanthracen-2,7,9,10-tetraone (I-h)

a) A solution of 4,6-dimethyl-1H-1,8-diazaanthracen-2,9,10-trione in trifluoroacetic acid (2 ml) and 30% hydrogen peroxide (1 ml) was agitated at 70° C. for 1 hour. Water (20 ml) was added and the cooled mixture was extracted with chloroform (75 ml), dried with $Na_2SO_4$ and evaporated at reduced pressure. The residue (0.22 g) was chromatographed over silica gel eluting with dichloromethane-ethanol (9:1) to give 130 mg. of 3-methyl-5-methyl-1H-1,8-diazaanthracen-7,9,10-trione 1-oxide (60%) m.p. 211° C.

Spectroscopic data for said N-oxide:

IR (KBr): 3200–2800 (NH), 1680, 1660, 1650 (C=O) cm$^{-1}$.

$^1$H-NMR(250 MHz, CDCl$_3$); 12.00 (s, 1H, NH); 8.52 (s, 1H, H-4); 7.77 (s, 1H, H-6); 2.54 (s, 3H, C$_5$—CH$_3$); 2.38 (s, 3H, C$_3$—CH$_3$) ppm.

b) Four portions of 50 mg. of tosyl chloride at 1-hour intervals were added to a solution of 85 mg. (0.30 mmol) of the above cited N-oxide in acetonitrile (25 ml) and water (4 ml.) The solution was agitated at 70° C. for 20 hours, cooled to room temperature and agitated with water (10 ml.) Diethyl ether was added and the red precipitate was filter and washed with ether yielding 60 mg (65%) of compound (I-h). m.p.>300° C. (dec.)

Spectroscopic data for compound (I-h):

$^1$H-NMR (250 MHZ, d$_6$)-DMSO): 6.78 (S, 1H, H-6); 7.82 (S, 1H, H-4); 2.10, 2.12 (2S 2×3H C$_{3,5}$—CH$_3$) ppm.

EXAMPLE 8

Preparation of 3,6-difluoro-1-8-diazaanthracen-9,10-dione (I-i)

A solution of benzoquinone (550 mg., 5.1 mmol) and 2-fluoro-propenal hydrazone (597 mg., 5.1 mmol) was refluxed for 18 hours in dry chloroform (25 ml.) After the solvent was evaporated at reduced pressure, silica gel column chromatography of the residue eluting with a dichloromethane-dicholormethane/ethyl acetate (4:1) gradient yielded the following identified compounds:

80 mg (8%) of 3-fluoro-6-dimethylaminoquinolin-5,8-dione;

32 mg (2%) of 3-fluoro-7-dimethylaminoquinolin-5,8-dione;

30 mg (5%) of 3-dimethylamino-6-fluoro-1,8-diazaanthracen-9,10-dione;

14 mg (3%) of 3,6-difluoro-1,8-diazaanthracen-9,10-dione (1-i) m.p. 236°–238° C.

Spectroscopic data for compound (1-i):

IR (KBr): 1710, 1680 and 1600 cm$^{-1}$.

$^1$H-NMR (250 MHz, CDCl$_3$); 9.02 (d, 2H, J=2.81 Hz, C$_2$-H and C$_7$-H); 8.30 (dd, 2H, J=7.48 and 2.84 Hz, C$_4$-H and C$_5$-H) ppm.

$^{19}$F-NMR (235 MHz, CDCl$_3$); 114.69 (d, J=7.6 Hz) ppm.

$^{13}$C-NMR (63 MHz, CDCl$_3$): 180.62 (C$_9$), 177.81 (C$_{10}$) 161.50 (C$_3$ and C$_6$, d J=270.1 Hz), 145.46 (C$_2$ and C$_7$, d, J=25.26 Hz) 145.04 (C$_{8a}$ and C$_9$ d J=4.59 Hz) 131.92 (C$_{4a}$ and C$_{10a}$) and 121.14 (C$_4$ and C$_5$, d J=19.62 Hz) ppm.

EXAMPLE 9

Preparation of 6-methyl-3-phenyl-1H-1,8-diazaanthracen- 1 2,9,10-trione (I-j)

a) A solution of phenylacetyl chloride (1.07 g, 6.6 mmol) in dry benzene (7 ml) was added drop by drop for 10 minutes to a cooled solution of 2,5-dimethoxyaniline (1 g, 6.5 mmol) in dry benzene (7 ml). The reaction mixture was agitated at room temperature for 1 hour and then the reaction was stopped with cold 24% aqueous sodium carbonate (10 ml.) After vigorously agitating the two-phase system for 30 minutes, the benzene layer was separated and the aqueous phase was extracted with ether (3×50 ml). The combined organic layers were dried over sodium sulfate and evaporated and the residue was crystallized from petroleum ether, yielding 1.61 g 91%) of N-(2',5'-dimethoxyphenyl)-2-phenylacetamide. m.p. 85° C. (petroleum ether).

Spectroscopic data for said phenylacetamide

IR (KBr): 3310 (NH), 1660 (C=O); 1220 (OCH$_3$) cm$^{-1}$.

$^1$H-NMR (300 MHz, CDCl$_3$) δ: 8.00 (1H, d, J=3.0 Hz, C$_6$-H); 7.80 (1H, s, N-H); 7.35 (5H, m, C$_6$H$_5$); 6.71 (1H, d, J=9.0 Hz C$_3$-H); 6.50 (1H dd J=9.0 and 3.0 Hz, C$_4$-H; 3.75 (3H, s, C$_5$—OCH$_3$); 3.65 (3H, s, C$_2$—OCH$_3$); 2.10 (2H s, C$_2$-H)ppm.

$^{13}$C-NMR (75.4 MHz, CDCl$_3$) δ: 168.89 (C$_1$); 153.89 (C$_5$); 142.00 (C$_2$); 134.45 (C$_{1'}$); 129.51 (C$_{2''}$, C$_{6''}$); 128.98 (C$_{3''}$, C$_{5''}$); 128.27 (C$_{1''}$); 127.42 (C$_{4'}$); 110.95 (C$_3$); 108.68 (C$_{4'}$); 105.56 (C$_6$); 56.29 and 55.73 (OCH$_3$); 45.13 (C$_2$) ppm.

b) Method A:

Phosphorous oxychloride (7.25 ml, 77 mmol) was added drop by drop to an agitated solution of N-(2'-5'-dimethoxyphenyl)-2-phenylacetamide (3 g., 11 mmol) in dimethylformamide (1 ml, 13 mmol), was kept under a nitrogen atmosphere and cooled for 14 hours at room temperature, while it was monitorized by fine layer chromatography (the desired product emitted a characteristic blue fluorescence upon exciting it at=366 nm). After the reaction has been completed, the solution was poured over chopped ice, basified with aqueous ammonia 25% and extracted with chloroform (3×50 ml.) The combined organic layers were dried (sodium sulfate) and evaporated and the residue was purified by means of flash column silica gel chromatography, eluting with petroleum ether-ethyl acetate 5:1. 800 mg. of 2-chloro-3-phenyl-5,8-dimethoxyquinoline (33%, calculated on the unrecovered starting amide) were obtained.

Method B

A mixture of phosphorous oxychloride (2.4 ml., 26 mmol, 7 eq) and dimethyl-formamide (0.43 ml., 5 mmol) was agitated at –302° C. for 15 minutes, while it was kept in a nitrogen atmosphere. Afterwards, N-(2', 5'-dimethoxyphenyl)-2-phenylacetamide (1 g., 3.7 mmol) in one portion was added and from this point the process was identical to the one described in Method A. Yield, 674 mg. of 2-chloro-3-phenyl-5,8-dimethoxyquinoline (77%). Afterwards it was subjected to silica gel column chromatography, eluting with petroleum ether-ethyl acetate-dichloromethane 6:1:1. m.p. 1252° C. (ethyl ether-petroleum ether)

Spectroscopic data for said dimethoxyquinoline:

IR (KBr): 1270 (OCH$_3$) cm$^{-1}$.

$^1$H-NMR (300 MHz, CDCl$_3$) δ: 8.49 (1H, s, C$_4$-H); 7.44–7.56 (5H, m, C$_6$H$_5$); 6.98 (1H, d, J=8.4 Hz, C$_7$-H); 6.79 (1H, d, J=8.4 Hz, C$_6$-H), 4.03 3H, s, C$_8$—OCH$_3$); 3.94 (3H, s, C$_5$—OCH$_3$) ppm.

$^{13}$C-NMR (75.4 MHz, CDCl$_3$) δ: 149.31 (C$_2$); 148.60 (C$_5$; 148.47 (C$_8$ ); 138.88 (C$_{8a}$); 134.39 (C$_4$); 134.11 (C$_3$); 137.83 (C$_{1'}$); 129.68 (C$_{2'}$ and C$_{6'}$); 128.15 (C$_{3'}$, C$_{5'}$ and C$_{4'}$); 120.55 (C$_{4a}$); 108.15 (C$_7$); 104.46 (C$_6$); 56.09 and 55.78 (OCH$_3$)

The interchangeable designations are designated with * c) A solution of 2-chloro-3-phenyl-5,8-dimethoxyquinoline (200 mg, 0.67 mmol) was refluxed for 3 hours in acetic acid (1.5 ml) and water (0.05 ml.) After the solvent was evaporated, the residue was dissolved in water, basified with aqueous ammonium hydroxide 25% and extracted with chloroform (3×25 ml). The combined chloroform layers were dried over sodium sulfate and evaporated, yielding an essentially pure residue of 187 mg (100%) of 3-phenyl-5,8-dimethoxy-2-(1H)-quinolinone. m.p. 207 (CDCl$_3$).

Spectroscopic data for said quinolinone:

IR (KBr): 1635 (C=O); 1250 (OCH$_3$) cm$^{-1}$.

$^1$H-NMR (300 MHz, CDCl$_3$) δ: 9.43 (1H, 2, NH); 8.27 (1H, s, C$_4$-H); 7.79 (2H, d, J=7.8 Hz, C$_2$-H and C$_6$-H); 7.40 (3H, m, C$_3$-H, C$_4$-H, and C$_5$-H); 6.87 (1H d, J=8.7 Hz, C$_7$-H); 6.51 (1H, d, J=8.7 Hz, C$_6$-H); 3.94 and 3.91 (6H, 2s, OCH$_3$) ppm.

$^{13}$C-NMR (75.4 MHz CDCl$_3$) δ: 161.14 (C$_2$; 149.87 (C$_5$); 139.39 (C$_8$); 136.36 (C$_4$); 132.85 (C$_{8a}$); 131.83 (C$_3$); 129.95 (C$_1$·); 128.79 (C$_2$· and C$_6$·); 128.12 (C$_3$· and C$_5$·); 127.93 (C$_4$·); 111.31 (C$_7$); 109.96 (C$_{4a}$); 101.08 (C$_6$); 55.75 and 55.63 (OCH$_3$) ppm.

d) Ammonium nitrate and cerium (241 mg, 0.435 mmol) were added in small portions to a magnetically agitated suspension of 3-phenyl-5,8-dimethoxy-2-(1H)-quinolinone (50 mg., 0.17 mmol) in water (0.8 ml) and acetonitrile (1.9 ml). The orange solution was agitated at 50° C. for 30 minutes and afterwards it was diluted with water (5 ml) and extracted with chloroform (3×20 ml), yielding 45 mg. (100%) of 3-phenyl-2,5,8-(1H)-quinolintrione. m.p. 185° C.

Spectroscopic data for said quinolintrione:

IR(KBr): 1645 (C=O) cm$^{-1}$.

$^1$ H-NMR (250 MHz, DMSO-d$_6$) δ: 12.20 (1H, s, NH); 7.91 (1H, s, C$_4$-H); 7.73 (2H, m, C$_2$-H and C$_6$-H); 7.43 (3H, m, C$_3$-H, C$_4$-H and C$_5$-H); 6.99 (1H, d, J=9.3 Hz, C$_7$-H); 6.92 (1H, d, J=9.3 Hz, C$_6$-H) ppm.

$^{13}$C$_7$-H); (75.4 MHz DMSO-d$_6$) δ: 183.17 (C$_8$); 179.93 (C$_5$); 161.00 (C$_2$); 141.77 (C$_{8a}$); 137.48 (C$_6$); 136.25 (C$_7$); 135.35 (C$_3$); 132.17 (C$_4$); 131.58 (C$_1$); 128.71 (C$_2$· and C$_6$·); 128.42 (C$_3$· and C$_5$·); 128.30 (C$_4$·); 114.39 (C$_{4a}$) ppm.

e) Methacrolein dimethylhydrazone (90 mg, 0.75 mmol) in one portion was added to a solution of 3-phenyl-5,8-dimethoxy-2-(1H)-quinolinone (190 mg, 0.71 mmol) in chloroform (50 ml.) The solution was agitated at room temperature for 3 hours and was evaporated. The residue was chromatographed over silica gel, eluting with ethyl acetate to give 120 mg (50%) of 6-methyl-3-phenyl-1H-1,8-diazaanthracen-2,9,10-trione (I-j). m.p. 275° C.

Spectroscopic data for compound (I-j):

IR(KBr): 1650 and 1660 (C=O) cm$^{-1}$.

$^1$H-NMR (250 MHz, CDCL$_3$) δ: 9.80 (1H, s, NH); 8.88 (1H, d, J=1.7 Hz, C$_7$-H); 8.36 (1H, d, J=1.4 Hz, C$_5$-H); 8.25 (1H, s, C$_4$-H); 7.80 (2H, m, C$_2$-H and C$_6$-H); 7.47 (3H, m, C$_3$-H, C$_4$-H and C$_5$-H); 2.57 (3H, s, C$_6$—CH$_3$) ppm.

$^{13}$C-NMR (75.4 MHz, CDCl$_3$) δ: 179.71 (C$_9$); 175.88 (C$_{10}$); 160.34 (C$_2$); 155.50 (C$_7$); 144.89 (C$_8$); 140.31 (C$_6$); 139.29 (C$_3$); 137.70 (C$_{9a}$); 140.31 (C$_6$); 139.29 (C$_3$); 137.70 (C$_{9a}$); 135.01 (C$_5$); 134.34 (C$_1$·); 132.59 (C$_4$); 129.69 (C$_4$ ); 129.48 (C$_{10}$); 128.70 (C$_2$ and C$_6$ ); 128.55 (C$_3$· and C$_5$·); 116.44 (C$_{4a}$); 19.17 (C$_6$—CH$_3$) ppm.

EXAMPLE 10

Preparation of 3-fluoro-4-methyl-1,4-dihydro-1-azaanthracen-9,10-dione (I-k)

A solution of naphthoquinone (553 mg, 3.5 mmol) and 2-fluoro-2-butenal N,N-dimethylhydrazone was refluxed for 8 days in chloroform (15 ml.) After the solvent was evaporated at reduced pressure, the residue was chromatographed over silica gel column, eluting with petroleum ether-ethyl acetate (9:1) and yielded 63 mg (10%) of compound (I-k) and 90 mg (15%) of 3-fluoro-4-methyl-1-azaanthracen-9-10-dione. m.p. 190°–192° C. (CDCl$_3$).

Spectroscopic data for compound (I-k).

IR (KBr): 3340, 1665, 1605 and 1595 cm$^{-1}$.

$^1$H-NMR (250 MHz, CDCl$_3$): 8.12 (dd, 1H, C$_8$-H); 8.04 (dd, 1H, C$_5$-H); 7.76 (dt, 1H, C$_6$H) 7.64 (dt, 1H, C$_7$-H); 6.54 (b.s. 1H, NH); 6.22 (m, 1H, C$_2$-H); 4.16 (m, 1H, C$_4$-H) and 1.37 (d 3H J=6.4 Hz C$_4$—CH$_3$) ppm.

$^{19}$F-NMR (235 MHz, CDCl$_3$): δ140.46 (t, J=7.5 Hz) ppm $^{13}$C-NMR (63 MHz, CDCl$_3$): 181.91 (C$_9$), 180.18 (C$_{10}$), 151.95 (C$_3$, d, J=253.59 Hz), 138.60, 133.46, 130.12 (C$_{8a}$, C$_{9a}$, C$_{10a}$) 134.85 (C$_7$) 132.32 (C$_6$) 126.27, 126.04 (C$_8$, C$_5$), 115.57 (C$_4$a, d, J=16.60 Hz), 106.31 (C$_2$, d, J=40.88 Hz), 29.95 (C$_4$, d, J=25.72 Hz), and 20.22 (C$_4$—CH3, d, J=3.46 Hz) ppm.

EXAMPLE 11

Preparation of 3-fluoro-1-azaanthracen-9,10-dione (I-1)

A solution of naphthoquinone (632 mg, 4 mmol) and 2-fluoro-2-propenal N,N-dimethylhydrazone was refluxed for 22 hours in dry chloroform (15 ml.) Another portion of naphthoquinone (0.41 g, 2.59 mmol) was added and the reflux continued for 3 more hours. After the solvent was evaporated at reduced pressure, silica gel column chromatography with elution with ethyl-ether-petroleum ether (1:1) yielded 187 mg (21%) of compound (I-1) and 42 mg (5%) of 3-fluoro-1,4-dihydro-1-azaanthracen-9,10-dione. m.p. 214° C. (MeOH).

Spectroscopic data for compound (I-1):

IR (KBr): 1700, 1680 and 1600 cm$^{-1}$.

$^1$H-NMR (250 MHz, CDCl$_3$): 8.95 (d, 1H, J=2.83 Hz, C$_2$-H); 8.44 (m, 1H, C$_8$-H); 8.34 (m, 1H, C$_5$-H) 8.29 (dd, 1H, J=7.74 and 2.83 Hz, C$_4$-H); and 7.89 (m, 2H, C$_6$-H and C$_7$-H) ppm.

$^{19}$F-NMR (235 MHz, CDCl$_3$): −116.06 (d, J=7.6 Hz) ppm.

$^{13}$C-NMR (63 MHz, CDCl$_3$): 181.68 (C$_9$), 180.06 (C$_{10}$) 161.28 (C$_3$ d J=268.5 Hz) 145.15 (C$_{4a}$, d, J=4.3 Hz), 144.23 (C$_2$, d, J=25.13 Hz), 135.08 and 134.58 (C$_6$ and C$_7$) 133.16 (C$_{8a}$) 132.59 (C$_{10a}$) 132.38 (C$_9$a, d, J=4.3 Hz), 128.07 and 127.35 (C$_5$ and C$_8$), 120.88 (C$_4$, d, J=19.26 Hz) ppm.

BIOLOGICAL ACTIVITY STUDIES

Antitumor tests

Cell cultures: The cells were kept in logarithmic phase of growth in Eagle's Minimum Essential Medium, with Earle's Balanced Salts, with L-gluatamine 2.0 mM, with non-essential amino acids and without sodium bicarbonate (EMEM-NEAA); supplemented with Fetal Calf Serum (FCS) 10% sodium bicarbonate 10$^{-2}$ and with 0.1 g/l penicillin-G+-streptomycin sulfate.

To determine and to compare the antitumor activity of these compounds, a simple screening process was carried out using an adapted form of the method described by Bergeron et al. (1984) ((1) Raymond J. Bergeron, Paul F. Cavanaugh, Jr., Steven J. Kline, Robert G. Hughes, Jr., Gary T. Elliot and Carl W. Porter. Antineoplastic and antiherpetic activity of spermidine catecholamide iron chelators. Biochem. Bioph. Res. Comm. 1984, 121 (3), 848–854; (2) Alan C. Schroeder, Robert G. Hughes, Jr. and Alexander Bloch. Effects of Acyclic pyrimidine nucleoside analogues. J. Med. Chem. 1981, 24, 1078–1083). The antitumor cells used have been P-388 (culture in DBA/2 mouse lymphoid neoplasm suspension), A-549 (human lung carcinoma monolayer culture); HT-29 human colon carcinoma monolayer culture) and MEL (human melanoma monolayer culture).

The P-388 cells were seeded in 16 mm cups at $1\times10^4$ cells per cup in aliquots at 1 ml. MEM 5FCS that contains the indicated drug concentration. Separately, a batch of cultures without any drug was seeded as a growth control to ensure that the cells were kept in a logarithmic phase of growth. All the determinations were carried out in duplicate. After three days of incubation at 37° C., 10% $CO_2$ in an atmosphere with 98% humidity, the approximate $IC_{50}$ was determined by comparing the growth in the cups with the drug and the control cups.

The A-549, HT-29 and MEL-28 cells were seeded in 16 mm cups at $2\times10$ cells per cup in aliquots of 1 mM of MEM 10FCS that contain the indicated drug concentration. Separately, a batch of cultures without any drug was seeded as a growth control to ensure that the cells were kept in a logarithmic phase of growth. All the determinations were carried out in duplicate. After three days of incubation at 37° C., 10% $CO_2$ in an atmosphere with 98% humidity, the cups were stained with crystal violet 0.1%. The approximate $IC_{50}$ was determined by comparing the growth in the cups with the drug and the growth in the control cups.

The results of the antitumor activity of the compounds described in the present specification appear in Table I.

TABLE I

| Compounds | $IC_{50}$ µg/ml | | | |
|---|---|---|---|---|
| | P-388 | A-549 | HT-29 | MEL-28 |
| (I-a) | 1 | 0,25 | 1 | |
| (I-b) | 5 | 0,25 | 10 | 5 |
| (I-c) | 0,1 | 0,025 | 0,1 | 0,1 |
| (I-d) | 1 | 0,25 | 1 | 0,25 |
| (I-e) | 0,005 | 0,02 | 0,05 | 0,05 |
| (I-f) | 0,02 | 0,02 | 0,02 | 0,02 |
| (I-g) | 0,5 | 0,05 | 0,05 | 0,1 |
| (I-h) | 0,05 | 0,05 | 0,05 | 0,025 |
| (I-i) | 0,025 | 0,1 | 0,1 | 0,025 |
| (I-j) | 2,5 | 5 | 10 | >10 |
| (I-k) | 0,25 | 0,25 | 0,25 | 0,12 |
| (I-l) | 0,25 | 0,05 | 0,25 | 0,05 |

We claim:
1. A compound of the general formula (I)

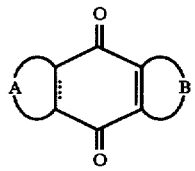

(I)

wherein the broken line represents an optional double bond, and A and B, together with the center ring, form an anthranquinonic system selected from the group consisting of

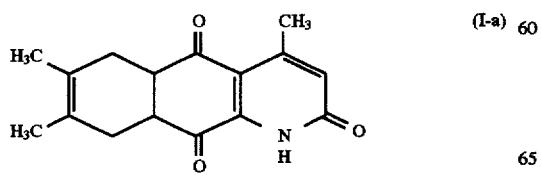

(I-a)

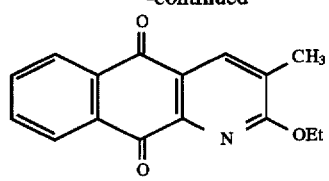

(I-b)

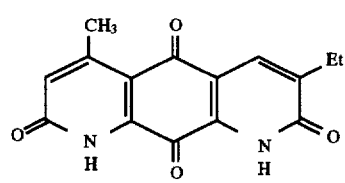

(I-c)

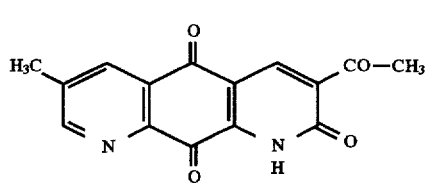

(I-d)

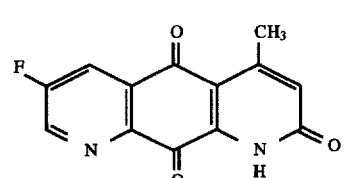

(I-e)

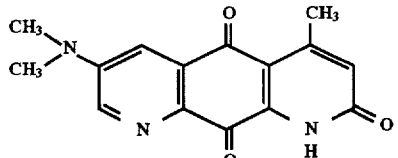

(I-f)

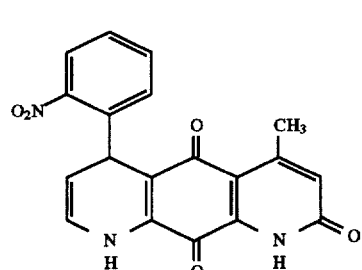

(I-g)

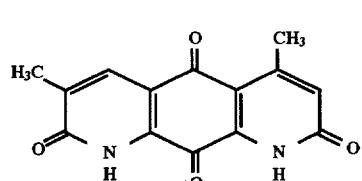

(I-h)

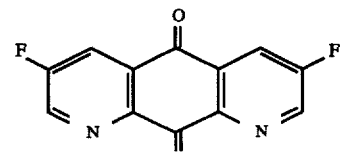

(I-i)

and

-continued

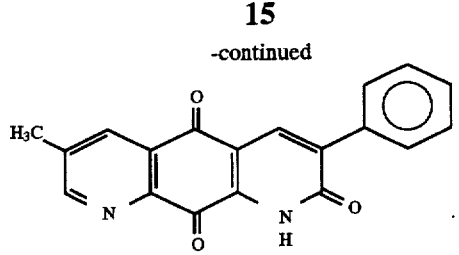

2. A compound derivative, accord to claim 1 of the formula (I-a):

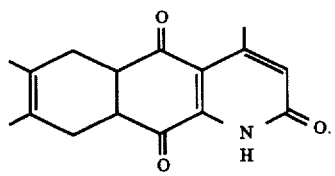

3. A compound derivative, according to claim 1 of the formula (I-b):

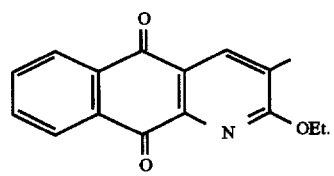

4. A compound derivative, according to claim 1 of the formula (I-c):

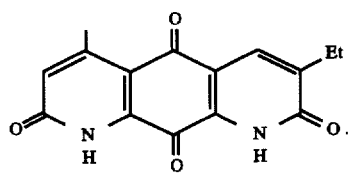

5. A compound derivative, according to claim 1 of the formula (I-d):

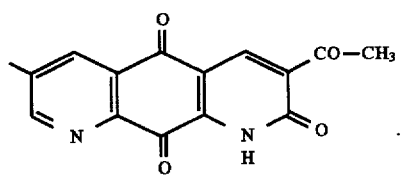

6. A compound derivative, according to claim 1 of the formula (I-e):

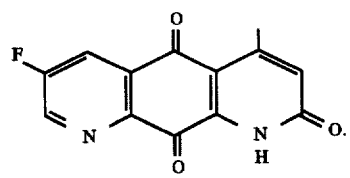

7. A compound derivative, according to claim 1 of the formula (I-f):

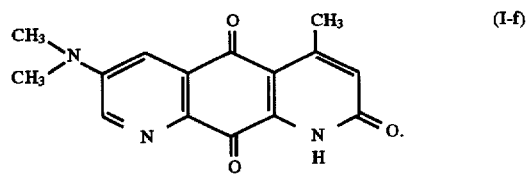

8. A compound derivative, according to claim 1 of the formula (I-g):

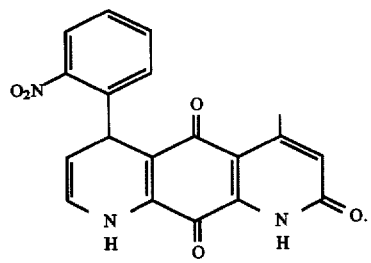

9. A compound derivative, according to claim 1 of the formula (I-h):

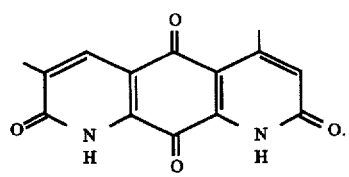

10. A compound derivative, according to claim 1 of the formula (I-i):

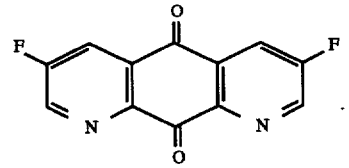

11. A compound derivative according to claim 1 of the formula (I-j):

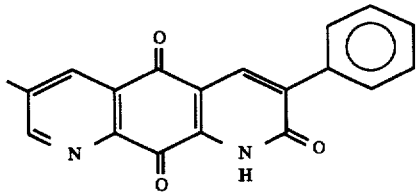

12. A method of inhibiting the growth of a tumor selected from the group consisting of leukemia, lung carcinoma, colon carcinoma and melanoma in a patient in need of such therapy which comprises administration of an antitumor mount of a compound of formula (I) of claim 1.

13. A method of inhibiting the growth of a tumor selected from the group consisting of leukemia, lung carcinoma, colon carcinoma and melanoma in a patient in need of such therapy which comprises administration of an antitumor mount of a compound of formula (1-a) of claim 2.

14. A method of inhibiting the growth of a tumor selected from the group consisting of leukemia, lung carcinoma, colon carcinoma and melanoma in a patient in need of such therapy which comprises administration of an antitumor mount of a compound of formula (I-b) of claim 3.

15. A method of inhibiting the growth of a tumor selected from the group consisting of leukemia, lung carcinoma, colon carcinoma and melanoma in a patient in need of such therapy which comprises administration of an antitumor amount of a compound of formula (I-c) of claim 4.

16. A method of inhibiting the growth of a tumor selected from the group consisting of leukemia, lung carcinoma, colon carcinoma and melanoma in a patient in need of such therapy which comprises administration of an antitumor amount of a compound of formula (I-d) of claim 5.

17. A method of inhibiting the growth of a tumor selected from the group consisting of leukemia, lung carcinoma, colon carcinoma and melanoma in a patient in need of such therapy which comprises administration of an antitumor amount of a compound of formula (I-e) of claim 6.

18. A method of inhibiting the growth of a tumor selected from the group consisting of leukemia, lung carcinoma, colon carcinoma and melanoma in a patient in need of such therapy which comprises administration of an antitumor amount of a compound of formula (I-f) of claim 7.

19. A method of inhibiting the growth of a tumor selected from the group consisting of leukemia, lung carcinoma, colon carcinoma and melanoma in a patient in need of such therapy which comprises administration of an antitumor amount of a compound of formula (I-g) of claim 8.

20. A method of inhibiting the growth of a tumor selected from the group consisting of leukemia, lung carcinoma, colon carcinoma and melanoma in a patient in need of such therapy which comprises administration of an antitumor amount of a compound of formula (I-h) of claim 9.

21. A method of inhibiting the growth of a tumor selected from the group consisting of leukemia, lung carcinoma, colon carcinoma and melanoma in a patient in need of such therapy which comprises administration of an antitumor amount of a compound of formula (I-i) of claim 10.

22. A method of inhibiting the growth of a tumor selected from the group consisting of leukemia, lung carcinoma, colon carcinoma and melanoma in a patient in need of such therapy which comprises administration of an antitumor amount of a compound of formula (I-j) of claim 11.

23. A pharmaceutical composition comprising a compound according to claim 1 together with a pharmaceutically acceptable carrier.

* * * * *